US009282759B2

(12) United States Patent
Msika et al.

(10) Patent No.: US 9,282,759 B2
(45) Date of Patent: Mar. 15, 2016

(54) COMPOSITION INCLUDING AN UNSAPONIFIABLE FRACTION

(75) Inventors: Philippe Msika, Versailles (FR); David Daguet, Leves (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 0 days.

(21) Appl. No.: 13/389,847

(22) PCT Filed: Aug. 12, 2010

(86) PCT No.: PCT/EP2010/061764
§ 371 (c)(1),
(2), (4) Date: Feb. 10, 2012

(87) PCT Pub. No.: WO2011/018501
PCT Pub. Date: Feb. 17, 2011

(65) Prior Publication Data
US 2012/0141387 A1 Jun. 7, 2012

Related U.S. Application Data

(60) Provisional application No. 61/235,728, filed on Aug. 21, 2009.

(30) Foreign Application Priority Data

Aug. 12, 2009 (FR) ..................... 09 55643

(51) Int. Cl.
| | | |
|---|---|---|
| *A61K 8/97* | (2006.01) | |
| *A61Q 11/00* | (2006.01) | |
| *A23L 1/30* | (2006.01) | |
| *A23L 1/302* | (2006.01) | |
| *A61K 36/00* | (2006.01) | |

(52) U.S. Cl.
CPC ........... *A23L 1/3006* (2013.01); *A23L 1/30* (2013.01); *A23L 1/3002* (2013.01); *A23L 1/302* (2013.01); *A23L 1/3004* (2013.01); *A23L 1/3008* (2013.01); *A61K 36/00* (2013.01); *A23V 2002/00* (2013.01)

(58) Field of Classification Search
USPC .......................................................... 424/58
See application file for complete search history.

(56) References Cited

U.S. PATENT DOCUMENTS

2003/0108650 A1* 6/2003 Kohler et al. ................. 426/601
2007/0116812 A1* 5/2007 Msika et al. ................. 426/417

FOREIGN PATENT DOCUMENTS

| | | |
|---|---|---|
| EP | 1 140 124 B1 | 10/2001 |
| EP | 1 530 430 B1 | 5/2005 |
| EP | 1 707 189 A2 | 10/2006 |
| EP | 1 762 247 A1 | 3/2007 |
| EP | 1 920 756 A1 | 5/2008 |
| FR | 1 434 955 A | 4/1966 |
| FR | 2 405 068 A1 | 5/1979 |
| FR | 2 648 347 A1 | 12/1990 |
| FR | 2 678 632 | 1/1993 |
| FR | 2 698 785 A1 | 6/1994 |
| FR | 2 724 663 A1 | 3/1996 |
| FR | 2 803 598 | 7/2001 |
| FR | 2 885 802 A1 | 11/2006 |
| FR | 2 887 749 A1 | 1/2007 |
| FR | 2 906 722 A1 | 4/2008 |
| JP | 52-148615 | 10/1977 |
| WO | WO 98/47479 A1 | 10/1998 |
| WO | WO 00/67726 A1 | 11/2000 |
| WO | WO 01/15552 A1 | 3/2001 |
| WO | WO 01/21150 A1 | 3/2001 |
| WO | WO 01/52873 A1 | 7/2001 |
| WO | WO 01/70046 A1 | 9/2001 |
| WO | WO 02/26207 A2 | 4/2002 |
| WO | WO 2004/019923 A1 | 3/2004 |
| WO | WO 2004/093869 A1 | 11/2004 |
| WO | WO 2005/112654 A2 | 12/2005 |
| WO | WO 2005/117827 A1 | 12/2005 |
| WO | WO 2006/021660 A1 | 3/2006 |
| WO | WO 2007/003762 A1 | 1/2007 |
| WO | WO 2007/009790 A1 | 1/2007 |
| WO | WO 2007/057439 A1 | 5/2007 |
| WO | WO 2008/006607 A2 | 1/2008 |
| WO | WO 2008/080974 A1 | 7/2008 |
| WO | WO 2011/012612 A2 | 2/2011 |

OTHER PUBLICATIONS

Cambazard et al, "Atopia: Atopic Dermatitis in More Than 3000 Young Children/Epidemiology and Management in Europe," Poster presented at 10th Meeting of Practical Pediatrics, Paris, France (3 pages)) (2006) available at http://www.mustelausa.com/professional/_images/pdfs/stelatopia_aad_poster.pdf.*
Lequesne et al., "Structural effect of avocado/soybean unsaponifiables on joint space loss in osteoarthritis of the hip," Database Caplus [Online], Chemical Abstracts Service, Database accession No. 2002:199920, Mar. 19, 2002.
Database WPI Derwent, Thomson Reuters, AN 1978-07543A Oct. 12, 1977 (abstract for JP52-148615).
International Search Report for PCT/EP2010/061764, mailed Aug. 19, 2011 (9 pages).

* cited by examiner

*Primary Examiner* — Dennis J Parad
(74) *Attorney, Agent, or Firm* — Foley & Lardner LLP

(57) ABSTRACT

The present invention relates to a composition, notably cosmetic, nutraceutical, dermatological, pharmaceutical or dietary, including at least one unsaponifiable extract, a drug including one such composition, the use of one such composition, a treatment method consisting in administering one such composition and a method comprising the administration of one such composition.

15 Claims, No Drawings

COMPOSITION INCLUDING AN UNSAPONIFIABLE FRACTION

The present invention relates to a composition, notably cosmetic, nutraceutical, dermatological, pharmaceutical or dietary, including at least one unsaponifiable extract. According to a particular embodiment the composition further includes an additional compound. This composition is intended in particular to treat, repair and/or prevent damage to conjunctive tissues in animals, in particular mammals, and most notably in human beings.

Conjunctive tissues are solid support tissues whose cells are separated by the extracellular matrix (ECM). These tissues are involved in support, protection, movement, inflammatory and immune response, and growth functions. The conjunctive tissues include various types of tissues such as cartilage, periodontium, skin, integuments and mucosae.

Notably in the case of the skin, mucosae and periodontium, fibroblasts or fibrocytes can be regarded as the principal cells of conjunctive tissue. They synthesise the protein and polysaccharide macromolecules of the conjunctive tissue ECM. They are also able to secrete many other molecules (cytokines, growth factors, enzymes) and play an important part in the processes of tissue repair and maintenance of inflammatory reactions.

In the case of cartilage, in particular articular cartilage, the chondrocytes can be regarded as the principal cells.

Conjunctive tissue thus includes cartilage and in particular articular cartilage, which is highly specialised conjunctive tissue with several structural and functional characteristics, in particular:
  it is free of blood and lymphatic vessels, as well as nerve structures,
  a single cell type is present, the chondrocyte, which not only ensures synthesis of the extracellular matrix of the cartilage, but also its regeneration.

Within the joint, cartilage is in contact by its deepest layer with subchondral bone and by its most superficial layer with synovial fluid.

In this articular cartilage, chondrocytes occupy roughly 5% to 10% of tissue volume. The number of chondrocytes decreases with age. Indeed, it seems that even if they remain very active metabolically, they no longer divide after adolescence.

Because of the avascular character of cartilage, chondrocytes consume great quantities of glucose (from the synovial fluid) to synthesise glucosamine, one of the major components of proteoglycans.

Each chondrocyte is to some extent a functional metabolic unit of the cartilage, isolated from nearby cells and responsible for the development and homeostasis of the components of the extracellular matrix which surrounds it.

This extracellular matrix is primarily comprised of water and molecules of aggrecan and type II collagen. Other molecules, which are in the minority, include type I, III, VI, IX, XI, XII and XIV collagens, hyaluronic acid and small leucine-rich proteoglycans.

One of the diseases related to cartilage, in particular articular cartilage, is osteoarthritis. This term covers a set of diseases of varied aetiology but whose semiology is common. A definition aiming at encompassing the principal facets of this disease was proposed by the World Health Organisation (WHO):

"Osteoarthritis is the result of mechanical and biological events that destabilise the balance between the synthesis and breakdown of cartilage and subchondral bone. This imbalance can be caused by multiple factors: genetic, congenital, metabolic or traumatic. Osteoarthritis affects all tissues of the diarthrodial joint and manifests itself by biochemical, molecular and biomechanical changes of the cartilaginous matrix leading to softening, cracking, ulceration and a loss of articular cartilage, sclerosis of the subchondral bone associated the formation of osteophytes and punched-out lesions. When it becomes symptomatic, osteoarthritis causes articular pain and stiffness, and potential articular effusion with variable degrees of local inflammation."

The speed and severity of cartilage breakdown are highly variable parameters of osteoarthritis. Moreover, cartilage destruction is not always linear but can be interrupted with phases of restoration of the joint space. The major symptom of osteoarthritis is pain.

The consequences of this disease are varied. First, the cartilage supporting stresses, in particular related to the weight of the body, breaks down when this disease is present. This breakdown is expressed in particular by a decrease in the thickness of the cartilage, which exposes the subjacent bone to greater stress than normal, and can lead to reshaping of the bone with the appearance of areas of osteoporosis and areas of bone condensation. This inhomogeneity of bone tissues can cause pain in surrounding tissues and also induce severe brittleness of bone tissues.

Moreover, tissue debris can form and accumulate within the joint, which can lead to an increase in the synthesis of proteolytic enzymes of cartilage breakdown such as collagenases, elastases, hyaluronidases, aggrecanases and metalloproteinases.

These enzymes can also act on cartilage not yet affected by the disease, causing lesions such as fissures of ulcers. The action of these enzymes can even involve the total and permanent disappearance of the cartilage, leaving the subjacent bone bare.

Lastly, intervention of the above-mentioned enzymes can induce secretion by surrounding tissues of chemical mediators including:
  primary cytokines such as interleukin 1 (IL-1) and tumour necrosis factor $\alpha$ (TNF-$\alpha$) or secondary cytokines such as IL-8 or IL-6, which are responsible for the appearance of an inflammatory reaction in the synovial membrane but also in the cartilage. The inflammatory reaction also causes pain and joint stiffness. Moreover, cytokines can not only lead to pain but also to oedemas. In addition, both major pro-inflammatory cytokines, IL-1b and TNF-$\alpha$, have significant effects on the chondrocyte. They are able to increase the synthesis of metalloproteinases or aggrecanases and inhibit the synthesis of components of the extracellular matrix such as collagen or aggrecan. IL-8 is directly involved in the production of catabolic enzymes and stimulates the production of PGE2. IL-6 decreases the production of type II collagen and aggrecan and acts with IL-1.
  eicosanoids such as prostaglandins, for example prostaglandin E (PGE), and leukotrienes B4 and C4, which are algogens. PGE2 has a catabolic role by supporting the breakdown of the extracellular matrix (ECM) and the expression of pro-inflammatory mediators.
  leukocyte adhesion proteins such as intercellular adhesion molecule 1 (ICAM-1).

Another type of conjunctive tissue is the periodontium. It includes the deep periodontium, alveolar bone, ligament, cementum, and the superficial periodontium, the gum. The gum is a specialisation of the oral mucosa.

Gingival conjunctive tissue includes cells and an extracellular matrix, just like the dermis.

The principal components of this tissue are collagen fibres (in general more than 60% of the area). Moreover, an elastic network represents several percent of the total proteins of the gum. Other non-collagen proteins are present in the gum, such as dermatan sulphate, chondroitin 4-sulphate, heparan sulphate, hyaluronic acid, as well as structure glycoproteins such as fibronectin, laminin, etc.

The primary cells that constitute it are fibroblasts. Mastocytes, leukocytes, monocytes, macrophages, lymphocytes and plasmocytes are also present.

The periodontium, and in particular the gum, thus includes an epithelium and conjunctive tissue. It is continuously attacked by physical, mechanical and biological agents. This is most notably why it is constantly restructuring: there is thus a dynamic equilibrium within this tissue. In particular this restructuring involves: macromolecules ensuring a matrix support for adhesion, proliferation and cell differentiation, cells ensuring their synthesis and/or breakdown, as well as proteases inhibitors able to break down these macromolecules.

Periodontal diseases include periodontopathy, periodontitis, a more severe form concerning the entire periodontium and characterised by bone loss, and gingivitis, a superficial affection limited to inflammation of the gum.

Gingivitis and periodontitis can be initiated by polymicrobial infections caused by bacteria in the plaque.

An initial lesion can be characterised by dilation of the vessels and leukocyte migration through the inter-epithelial space of the junctional epithelium and can lead to considerable collagenic and elastolytic lysis. Inflammation of the periodontium can result in the destruction of conjunctive tissue and optionally tooth loss.

Breakdown of the extracellular matrix during periodontal disease can be due to the host response by synthesis of inflammation mediators able to activate in the host a protease activation cascade.

All these phenomena constitute gingivitis. Periodontitis starts when there is destruction of the alveolar bone and apical migration of the junctional epithelium. Types of periodontitis include prepubertal periodontitis, juvenile periodontitis, rapidly progressive periodontitis, adult periodontitis, generalised aggressive periodontitis, localised aggressive periodontitis, and chronic periodontitis.

Another type of conjunctive tissue includes the skin, mucosae and integuments (hair, nails). These tissues are particularly prone to ageing. This ageing leads to dermatological problems more frequent in the aged, related to the fact that the skin has been exposed longer to a more or less cumulative amount of UV rays, "extrinsic" or "photo-induced" ageing, but also to changes of the structures of the skin itself over time, "intrinsic" or "chronological" ageing, in particular on the level of conjunctive tissues.

Ageing can also lead to a reduction in the vascularization of the dermis, which can cause disturbances of thermoregulation, as well as weakening of dermal clearance capacity (elimination of foreign toxin) which is the source of certain dermatoses such as contact dermatitis.

Ageing also leads to a decrease in the skin's thickness and elasticity, which can explain the appearance of bags under the eyes, cutaneous lines and wrinkles, as well as accentuation of dermal lesions during trauma.

For example, "mature skin" can be characterised by changes in the hypodermis, the dermis and/or the epidermis: the hypodermis gradually disappears, the dermis gets thinner and the conjunctive tissue loses its fibrous structure and its capacity to retain water. Elastic fibres break down and wrinkles appear.

Endogenous factors include the following: reduced cell regeneration capacity, reduced activity of sebaceous and sudoriparous glands, reduced production of oestrogen.

Exogenous factors of ageing include UV exposure, use of alcohol and/or tobacco, as well as the influence of climate, time and pollution.

In addition, tissue lesions induce an inflammatory reaction whose goal is to eliminate the attacking agent and necrotic tissues in order to allow the repair of damaged tissues. This repair can be imperfect and lead to the replacement of destroyed tissues by a fibrous scar. This process is called connective organisation of the focus of inflammation: it leads to the appearance of scars.

These scars can be the cause of severe morphological and functional disorders. Among the various types of scars, hypertrophic scars and retractile scars can be cited in particular.

Certain factors influence the quality of scarring, such as age, poor nutrition, immune deficiencies, a defect in local vascularization, etc.

However, it is also possible to link the quality of conjunctive tissues with the quality of scarring.

In addition, during exaggerated distensions of the skin or hormonal changes, stretch marks, or cutaneous striae, can appear. The principal triggering factors are inflammation, mechanical stress, and hormonal environment. All of these factors cause stretching, disorganisation of elastin and collagen fibres, without the rupture of supporting tissue. The major cause of elastic rupture comes from a lack of water in the cells. Stretch marks are on the whole comparable to atrophic scars.

The present invention aims at fighting against breakdowns, often inflammatory in nature, of conjunctive tissues, notably cartilages, periodontium, skin, mucosae and integuments. It more particularly aims at fighting against the effects of ageing and the breakdown of conjunctive tissues, at improving scarring, as the case may be fighting against stretch marks, and fighting against the inflammation of conjunctive tissues, notably cartilages and/or periodontium, as well as promoting the synthesis of the extracellular matrix (ECM) and/or maintaining the homeostasis of the extracellular matrix.

The invention can act to prevent, repair and/or treat damaged conjunctive tissues, in particular inflamed tissues, notably in the case of cutaneous lesions, in particular related to ageing such as wrinkles and lines, as well as stretch marks, in the case of lesions of the periodontium, with for example gingivitis and periodontopathy and/or in the case of cartilage lesions, for example osteoarthritis.

Although many compounds may have already been proposed to solve these problems, they have disadvantages in general, such as secondary and/or undesirable effects, high cost, limited shelf life, required doses that are too large and/or insufficient effects.

The aim of the invention is thus to allow connective tissues, in particular broken-down, injured or inflamed tissues, to be repaired and/or to decrease or eliminate the "undesirable" effects of the inflammation, in particular pain, while solving in whole or part the problems stated in the present description.

According to a first aspect, the invention has as an aim a composition, notably dietary, nutraceutical, cosmetic, pharmaceutical or dermatological, including at least one unsaponifiable fraction.

According to an embodiment the invention has as an aim a composition, as disclosed in claim 1.

This composition can notably prevent or treat diseases of connective tissues, notably of the cartilage, gums and cutaneous dermis, most particularly osteoarthritis, periodontopathy, all or part of the effects of ageing of the skin, such as wrinkles, all or part of the effects related to tissue damage and/or inflammation, such as scars or stretch marks.

The inventors noted that the compositions as described in the present description possess improved properties, notably in terms of lower dosing, improved effectiveness, improved tolerance and/or lower cost of obtaining the aforesaid composition.

The unsaponifiable of a fatty substance includes all of the components that after hydrolysis under basic conditions (saponification) are virtually insoluble in water and soluble in organic solvents (ethyl ether, aliphatic or aromatic hydrocarbons, chlorinated solvents, etc.).

According to another way of classifying the components, an unsaponifiable portion can include two types of compounds:

non-hydrolysable compounds, called the "non-hydrolysable portion", which includes among other things hydrocarbons, tetraterpene compounds or fatty alcohols or triterpene compounds present in free form, in other words with the alcohol function not esterified by a fatty acid, and, hydrolysed compounds, called the "hydrolysed portion", from hydrolysable compounds including mainly sterol esters, waxes and tocopherol esters.

An unsaponifiable portion can thus include non-hydrolysable components of the fatty substance, as well as those resulting mainly from the saponification of fatty acid esters, such as sterol esters, waxes and tocopherol esters.

In the context of the present invention, "unsaponifiable fraction" may means all or part of a fatty substance which contains at least the non-hydrolysable portion an unsaponifiable portion, and optionally the hydrolysed portion of an unsaponifiable portion.

Thus, an unsaponifiable fraction can notably be:

an oil, notably refined or crude, concentrated in compounds belonging to the unsaponifiable, in particular in non-hydrolysable compounds, notably an oleodistillate or a concentrate, a total unsaponifiable, notably crude or treated, in other words the totality of the compounds resulting from the hydrolysis of one of the oils cited above, compounds which are virtually insoluble in water and soluble in organic solvents, a portion of the total unsaponifiable, notably crude or treated, in particular the hydrolysable portion or the non-hydrolysable portion, and/or, at least one specific family or compound coming from the total unsaponifiable or from a portion of the total unsaponifiable or a derivative of said compound.

In the context of the present invention, "oleodistillate" or "concentrate" means an oil, crude or refined, with a content at least two times, in particular at least five times, more particularly at least eight times, or at least ten times greater in compounds belonging to the unsaponifiable portion than the oil, crude or refined, or the fatty substance from which it arises.

In particular, a portion of the total unsaponifiable means that an amount of about 30 to 99% by weight, in particular about 30 to 95% by weight, more particularly about 30 to 90% by weight and even more particularly about 30 to 80% by weight of the total weight of the total unsaponifiable.

By "family coming from the total unsaponifiable or from a portion of the total unsaponifiable" is meant a group of compounds which are from the same chemically family, examples of such family can be saturated or unsaturated hydrocarbons, aliphatic or terpenic alcohols, sterols, tocopherols, carotenoid pigments and xanthophiles, more particularly, the furanic lipids, as for example in the avocado unsaponifiable.

Of course, the unsaponifiable fraction can include, or be comprised of, at least one oleodistillate. More particularly, the unsaponifiable fraction consists of one or two oleodistillates.

The fatty substance, or oil, that can be used in the present invention can be obtained via one of the following extraction methods:

physical extraction, such as cold pressing on a mechanical press, pressing on a twin-screw extruder, separation by decantation and centrifugation;

chemical extraction using organic solvents (aliphatic alkanes, alcohols, chlorinated solvents, fluorinated solvents);

extraction in a supercritical medium, using carbon dioxide alone and/or with co-solvents.

Most particularly, the method for obtaining an unsaponifiable fraction can include the steps of the method described in the French patent application FR 2,803,598.

The material from which the fatty substance is extracted can be fresh or more or less dried. If it is dried, drying can be carried out for example by a stream of hot air or by lyophilisation.

The oil or fatty substance, before extraction of the unsaponifiable portion, can be refined or not. Refining possibilities include degumming, neutralisation, discolouration, deodorisation and winterization, also called demargarinating.

Each of the various steps cited above relating to extraction, drying and refining can have an impact on the composition of the unsaponifiable portion, as much in terms of quantity and the ratio between the compounds as in terms of the compounds belonging to the unsaponifiable portion.

In addition, in the method for obtaining an unsaponifiable fraction, the fatty substance or oil can be subjected to steps of fractionation or concentration. These steps can play a role in the composition of the unsaponifiable fraction produced. Such operations can be intermediate steps insofar as they can be used to limit the quantities to be saponified in the hydrolysis step or the specific steps for preparing unsaponifiable-enriched unsaponifiable fractions.

In addition, the source of origin of the fatty substance or oil leads to unsaponifiable fractions whose compositions can be quite different.

The fatty substance or oil can come from various sources, in particular from organisms, such as plants, animals or unicellular organisms. This fatty substance can also come from mineral compounds, such as mineral waxes.

More particularly, the fatty substance comes from oils of plant origin, oils of animal origin, oils of unicellular organisms, and waxes of mineral, plant or animal origin.

Oils of plant origin include oils from seeds and fruits, and in particular from avocado, canola, maize, sunflower, sesame, lupin, soya and/or avocado, notably from avocado and/or soya.

Oils of animal origin can come from animal fats, such as lard, tallow, bone fats, poultry fats, egg fats, dairy fats and fish oils.

Oils of unicellular organisms can come from yeasts, fungi, bacteria and algae.

According to a particular embodiment, the unsaponifiable fraction includes at least one extract of ovine, bovine and/or caprine cartilage, sea cucumber and/or green mussels.

According to another particular embodiment, the unsaponifiable fraction includes, or is comprised, of at least one oil, crude or refined, concentrated in compounds belonging to the unsaponifiable portion, coming from avocado, canola, maize, sunflower, sesame, lupin, soya and/or avocado, in particular from avocado and soya.

According to still another particular embodiment, the unsaponifiable fraction includes, or is comprised of, at least one total unsaponifiable, notably coming from avocado, canola, maize, sunflower, sesame, lupin, soya and/or avocado, in particular from avocado and soya.

More particularly the unsaponifiable fraction includes, or is comprised of, at least two, notably two total unsaponifiables, still more particularly these unsaponifiables come from avocado and soya, notably the formulas Avosol®, Avovida®, Avocadin®, Avosterol®, Avocadox® and NMX 1000®.

Quite particularly, the unsaponifiables of avocado and soya include a mixture of unsaponifiables, notably of total unsaponifiable, of avocado, in particular furanic, and of unsaponifiable, notably total, of soya, in particular in a ratio ranging from ⅓ to ⅔, still more advantageously the product in question can be Piascledine® marketed by Expanscience Laboratories.

An unsaponifiable fraction coming from lupin can be obtained according to international application WO 98/47479. This fraction advantageously contains 60% by weight of unsaponifiable.

An unsaponifiable fraction coming from sunflower can be obtained from linoleic sunflower, such as the active Solin® marketed by Expanscience Laboratories, and as described in international application WO 01/21150.

According to still another variant, the composition includes at least one compound or a derivative of same present in the unsaponifiable, such as for example that described in the European patent application EP 1,530,430 for obtaining an avocado unsaponifiable rich in furanic lipids.

Included among unsaponifiable fractions are avocado furanic lipids, in particular as described in international application WO 01/21605.

The content of the unsaponifiable fraction can range from 0.01% to 20% by weight, notably from 0.05% to 15% by weight, in particular from 0.1% to 5% by weight compared to the total weight of the composition.

The composition can include at least one additional compound. This compound can improve the properties, notably the activity of the inventive compositions. Quite particularly, the additional compound can improve the properties of the composition, or can provide a synergy with the unsaponifiable fraction, notably with respect to the treatment, repair and/or prevention of the damage to connective tissues, in particular in the prevention, repair or treatment of connective tissue diseases, such as osteoarthritis, periodontopathy or gingivitis, or of skin problems, cutaneous damage or stretch marks. This compound can in particular provide an improvement or a synergy with respect to the action of the composition on the inflammation of connective tissue.

The additional compound can be selected from:
essential fatty acids,
vitamins,
ingredients active in diseases such as osteoarthritis or periodontopathy, such as diacerein,
carotenoids and xanthophylls,
methylsulfonyl methane and S-adenosylmethionine,
chlorogenic acid,
mono- and di-glycerol glycosides,
boswellic acid,
curcuminoids, for example via an extract of *Curcuma longa*,
phenols and polyphenols,
polysaccharides,
minerals and/or trace elements,
probiotics and/or prebiotics,
anti-inflammatories,
anti-metalloproteases,
anti-VEGF (vascular endothelial growth factor), anti-NGF (nerve growth factor), and anti-NO (nitric oxide),
pain relievers,
bone drugs
plant extracts,
antioxidants, notably sulphurated,
antibacterials,
antifungals,
fullerenes, notably water-soluble, lignans, phytoecdysones, lutein, amino acids such as phenylalanine, leucine, natural or non-natural PPAR agonists, lipolytics, anti-lipogenics, guggulipids, guggulsterones, osteoprotegerin, diacerein and primorine,
aminated sugars,
anti-inflammatories/anti-irritants, soothing agents,
antioxidants, sun screens,
agents that heal and restructure the cutaneous barrier,
anti-ageing agents,
antifungals,
antiseptic and/or antibacterial preservatives,
antibiotics,
pseudo-preservatives, and,
agents that prevent hair loss and/or strengthen the hair and nails.

According to a first variant, the composition further includes at least one additional compound selected from:
essential fatty acids,
vitamins,
ingredients active in the disease of osteoarthritis or periodontopathy, such as diacerein,
carotenoids and xanthophylls,
methylsulfonyl methane and S-adenosylmethionine,
chlorogenic acid,
mono- and di-glycerol glycosides,
boswellic acid,
curcuminoids, for example via an extract of *Curcuma longa*,
phenols and polyphenols,
polysaccharides,
minerals and/or trace elements,
probiotics and/or prebiotics,
anti-inflammatories,
anti-metalloproteases,
anti-VEGF (vascular endothelial growth factor), anti-NGF (nerve growth factor), and anti-NO (nitric oxide),
pain relievers,
bone drugs
plant extracts,
antioxidants, notably sulphurated,
antibacterials,
antifungals,
fullerenes, lignans, phytoecdysones, lutein, amino acids such as phenylalanine, leucine, natural or non-natural PPAR agonists, lipolytics, anti-lipogenics, guggulipids, guggulsterones, osteoprotegerin, diacerein and primorine, and,
aminated sugars.

Additional essential fatty acid components can be present in the composition via at least one oil, or an oil fraction, in particular not enriched in the compound belonging to the unsaponifiable, chosen among the following oils: algae, avocado, canola, raspberry, kiwi, blackberry, palm, red palm, fish, sesame, soya, sunflower, *Echium*, haref, olive, maize, fish, shellfish and zooplanktons, in particular rich in ω-3, such as krill oil.

The composition can include at least one vitamin, for example C, D, E, K2 and group B. This vitamin can be supplied by a natural raw material extract, such as Acerola, *Citrus* fruits, Camu Camu, soya, cereals, yeasts, or can be obtained by synthesis.

Carotenoids and xanthophylls, notably astaxanthin, cryptoxanthin, lutein, lycopene and zeaxanthin, can for example be present in the composition via oil extracts of plant flowers, algae or krill oil, or can be obtained by synthesis.

When the composition includes at least one chlorogenic acid, it can be present in the form of an extract of raw coffee or of other plants.

The composition can include at least one mono- and diglycerol glycoside, for example via an extract of berries of rose hips or *Rosa canina*.

Aminated sugars that can be used are notably: glucosamine hydrochloride, chondroitin sulphate, type II collagen, hydrolysed or not, glucosamine, glycosaminoglycan, glycosaminoglycan polysulphates, collagen hydrolysates, N-acetyl glucosamine, glucosamine phosphate, glucosamine sulphate and/or hyaluronic acid, but also protein hydrolysates of the matrix (collagen).

Quite particularly, amino sugars can be obtained from cartilages, notably from animals and/or plants, in particular marine animals or plants, or from biotechnologies.

Boswellic acid can be present in an extract of *Boswellia serrata* and the curcuminoids in an extract of *Curcuma longa*.

Polyphenols can include or consist of at least one compound chosen among procyanidolic oligomers (PCOs), resveratrol, procyanidins, catechins, cyanidins and tannins, notably resveratrol. These polyphenols can for example be present via extracts of bark of maritime pine, garlic, onion, olive-tree leaf, olive, grape, grape seed, mangosteen, green tea, acai, Acerola, Aronia or blackcurrant.

Phenols can be compounds in which phenolic alcohol is in the alpha position of a methoxy group, in particular they can belong to the family of vanilloids, for example selected from gingerol, shogaol and capsaicin. Other phenols make up the family of lignans (flax or will schisandra).

When gingerol, shogaol or capsaicin is present, it can come from extract of ginger or pepper or *capsicum*.

Other antioxidants, notably sulphurated, can be included such as cysteine, methionine or glutathione or carbon-bearing molecules such as fullerenes.

Polysaccharides come for example from extract of berries of goji, Acerola and/or Camu Camu.

Minerals and/or trace elements can notably be calcium, copper, zinc, gold and derivatives, silver and manganese.

Probiotics can be present in the form of lactic ferments and can be living or not.

Prebiotics are generally short-chain oligosaccharides or polysaccharides comprised of roughly two to twenty sugar units. They escape digestion in the small intestine and are potential substrates for hydrolysis and fermentation by intestinal bacteria.

Prebiotics can act as a selective substrate of one or more, in general a limited number, of beneficial bacterial strains that reside in the colon and stimulate bacterial growth. Bifidobacteria and lactobacilli are microorganisms of the intestinal microbiota, or intestinal flora, most frequently targeted.

Prebiotics can be found naturally in fruits and vegetables and are extractable, for example inulin. Others are commercially produced by hydrolysis of polysaccharides, for example fructooligosaccharides or oligofructoses, or are synthesised by subjecting disaccharides such as lactose to the action of enzymes such as lactases with transferase activities to produce trans-galactooligosaccharides or by a chemical reaction of isomerisation which yields lactulose. Currently, trans-galactooligosaccharides and fructans such as inulin are those whose prebiotic effects are particularly recognised.

Anti-inflammatories can be selected from NSAIDs, notably anti-cyclooxygenase, or anti-COX, and/or anti-lipoxygenase, or anti-LOX, the anti-inflammatory cytokines, such as tumour necrosis factor alpha (TNF-α).

Anti-metalloproteases are notably the anti-ADAMTS family (anti-aggrecanases).

Anti-VEGF agents, such as genistein, extract of Ambora, escin, esculoside, ivy and ruscus, or anti-NGF, anti-NO, for example the extracts of olive tree or green tea, more particularly $N^G$-monomethyl-L-arginine, abbreviated NMMA, $N^G$-nitro-L-arginine methylated ester, abbreviated NAME, $N^G$-nitro-L-arginine, abbreviated NNA, $N^G$-amino-L-arginine, abbreviated NAA, $N^G$-dimethyl-arginine, asymmetrical dimethylarginine, abbreviated ADMA, diphenyleneiodonium chloride, 2-(4-carboxyphenyl)-4,4,5,5-tetramethylimidazoline-1-oxy-3-oxide, 7-nitroindazole, N(5)-(1-iminoethyl)-L-ornithine, aminoguanidine, canavanine and ebselen.

Pain relievers are for example selected from tramadol, paracetamol, salicylic acid and opioids.

Bone drugs can be biphosphonates or strontium ranelate.

Plant extracts notably can be selected from rhubarb extracts, in particular including diacerein, or diacetylrhein, and/or primorine, *Morinda citrifolia*, green tea, *Centella asiatica*, *Alpinia galanga*, algae, for example Aquamin™ which is an extract of *Lithothamnium calcareum*, fruit of milk thistle, containing sylimarin or quercetin, and Xianlinggubao Chinese plants such as *Epimedium, Dipsacus* root, *Salvia* root, *Anemarrhena* root, *Psoralea* seed and *Rehmannia* root.

Plant extracts can further be selected from clover soya isoflavones, soya proteins, *Opuntia* polysaccharides, *Boswellia* resin, *Perna* canaliculus, such as Lypirinol® and extracts of sage and willow or meadowsweet.

The plant extracts can also exhibit anti-inflammatory activity, notably if they are from *Rosa canina, Clematis manshurica, Phellodendron, Citrus, Whithania somnifera*, parthenolides, *Garcinia kola, Arnica*, ginger and/or *Harpagophytum*.

Other additional compounds can be mentioned, for example phytoecdysones, amino acids, notably phenylalanine and leucine, natural or non-natural PPAR agonists, lipolytics, anti-lipogenics, guggulipids, sterones and osteoprotegerin.

Antibacterials and/or antifungals in particular can be present for topical application, notably for oral application.

The additional compound particularly can be selected from vitamin K2, fish, zooplankton or shellfish oils, notably rich in ω-3 fatty acids, such as krill oil, hyaluronic acid, polyphenols, diacerein, notably in the form of rhubarb extract, methylsulfonyl methane and S-adenosylmethionine, extracts of plants such as *Harpagophytum*, mangosteen and ginger, coenzyme QH and coenzyme Q10.

According to a particular embodiment, the composition includes at least one avocado and soya total unsaponifiable, also called ASU, such as Avosol®, Avovida®, Avocadin®, Avosterol®, Avocadox®, NMX 1000® and Piascledine®, with at least one additional compound selected from vitamin K2, fish or zooplankton oils, notably rich in ω-3 fatty acids, hyaluronic acid, diacerein, coenzyme Q10, coenzyme QH and plant extracts.

According to another particular embodiment, the composition includes at least one oleodistillate selected from avocado, soya, avocado and soya, maize, canola, palm, sunflower with at least one additional compound selected from vitamin K2, fish or zooplankton oils, notably rich in ω-3 fatty acids, hyaluronic acid, diacerein, coenzyme Q10, coenzyme QH or plant extracts.

According to still another particular embodiment, the composition includes at least one plant phytosterol, arising from the unsaponifiable fraction, with at least one additional compound selected from vitamin K2, fish or zooplankton oils, notably rich in ω-3 fatty acids, hyaluronic acid, diacerein, coenzyme Q10, coenzyme QH, ubiquinol, and plant extracts.

In the context of the present application, "oil rich in ω-3 fatty acids" means oil including at least 5% by weight, notably at least 10% by weight, in particular at least 15% by weight, or at least 20% by weight of ω-3 fatty acids compared to the total weight of oil.

According to another of its aspects, the invention has as an aim a drug including, or comprised of, an unsaponifiable fraction and at least one additional compound such as defined in the present description and in particular as described above.

According to still another of its aspects, the invention has as an aim the use of a composition including at least one unsaponifiable fraction and at least one additional compound such as defined above for the preparation of a drug.

Quite particularly, this drug is intended to treat or prevent disorders related to the breakdown of connective tissue, notably osteoarthritis, gingivitis and periodontopathy and/or to repair the damage caused by these diseases.

Still more particularly, the drug is used to fight against connective tissue inflammation.

According to a second variant the additional compound can be selected from:
  anti-inflammatories/anti-irritants, soothing agents,
  antioxidants, sun screens,
  agents that heal and restructure the cutaneous barrier,
  anti-ageing agents,
  antifungals,
  antiseptic preservatives,
  antibiotics,
  pseudo-preservatives, and,
  agents that prevent hair loss and/or strengthen the hair and nails.

In this second variant, the composition is more particularly intended for use on the skin, mucosae and integuments, notably via topical or oral application.

The anti-inflammatory, anti-irritant and soothing agents can limit the inflammatory reaction, notably led via cytokines or mediators of the metabolism of arachidonic acid and exhibit soothing and anti-irritating properties.

Such agents include glycyrrhetinic acid, notably liquorice derivatives, such as the salts and esters of same; lipoic acid; beta-carotene; vitamin B3, such as niacinamide and nicotinamide; vitamin E; vitamin C; vitamin B12; flavonoids, for example green tea, quercetin, etc.; lycopene or lutein; avocado sugars; avocado oleodistillate; arabinogalactan; lupin peptides; total lupin extract; peptide extract of quinoa; Cycloceramide® which is an oxazoline derivative; isoflavones such as for example genisteine/genistine and daidzeine/daidzine; spring or thermal water, such as Avène water, Roche Posay water, Saint Gervais water, Uriage water, Gamarde water; extracts of goji or *Lycium barbarum*; plant peptides or amino acid complexes; topical disulone; steroidal anti-inflammatory drugs (SAIDs), such as corticoids, or non-steroidal anti-inflammatory drugs (NSAIDs).

Antioxidants can be a molecule that decreases or prevents the oxidation of other chemical substances.

Antioxidants can be selected from the group comprised of thiols; phenols; liquorice derivatives, such as glycyrrhetinic acid and the salts and esters of same; alpha bisabolol; extract of *ginkgo biloba* or *calendula*; Cycloceramide®, oxazoline derivative; avocado peptides; trace elements such as copper, zinc, and selenium; lipoic acid; vitamin B12; vitamin B3, notably niacinamide and/or nicotinamide; vitamin C; vitamin E; coenzyme Q10; krill; glutathione; BHT (butylhydroxytoluene); BHA (butylhydroxyanisol); lycopene or lutein; beta-carotene; polyphenols such as tannins, phenolic acids, anthocyanins, flavonoids, with for example green tea extracts, red fruits, cocoa, grape, *Passiflora incarnata, Citrus*; isoflavones such as for example genisteine/genistine and daidzeine/daidzine.

Antioxidants can further be selected from anti-glycation substances, such as carnosine; sulphur amino acids such as N-acetyl-cysteine, methionine, glutathione; antioxidant or antiradical enzymes such as SOD (superoxide dismutase), catalase, glutathione peroxidase, thioredoxin reductase and agonists thereof.

Agents that heal and restructure the cutaneous barrier can stimulate the synthesis of key lipids of the epidermis.

These agents that heal and restructure the cutaneous barrier can be selected from vitamin A; panthenol, vitamin B5; avocado sugars; lupeol; peptide extract of maca; peptide extract of quinoa; arabinogalactan; zinc oxide; magnesium; silicon; madecassic or asiatic acid; dextran sulphate; coenzyme Q10; glucosamine and derivatives of same; chondroitin sulphate and glucosaminoglycans or GAG; ceramides; cholesterol; squalane; phospholipids; fermented or non-fermented soya peptides; plant peptides; marine, plant or biotechnological polysaccharides such as extracts of algae or extract of fern; trace elements; extracts of tannin plants, such as tannins deriving from gallic acid called gallic or hydrolysable tannins, initially found in gall nut, catechin tannins arising from the polymerization of flavan units whose model is provided by catechu (*Acacia catechu*).

Trace elements of use are advantageously selected from the group comprised of copper, magnesium, manganese, chromium, selenium, silicon, zinc and mixtures thereof.

Agents that heal and restructure the cutaneous barrier can further be selected from sunflower concentrates, more advantageously linoleic sunflower concentrates, such as the active ingredient marketed by Expanscience Laboratories, Soline®, plant oil unsaponifiables, such as Avocadofurane®, modulators, notably agonists of:
  PPAR (peroxisome proliferator-activated receptor), such as rosiglitazone and pioglitazone,
  RXR (retinoid X receptor), such as retinoic acid and retinol retinaldehyde, and/or,
  LXR (liver X receptor), notably oxysterol or oxidised cholesterol.

Anti-ageing agents can act in combination for the treatment of middle-aged subjects with acne. These agents can be antioxidants, notably vitamin C, vitamin A, retinol, retinal, vitamin B3, AHA, such as lactic or glycolic acid, or BHA, such as salicylic acid, hyaluronic acid, of any molecular weight, Avocadofurane®, lupin peptides or peptide extract of maca.

Antifungals can be econazole, ketoconazole or zinc pyrithione.

Antiseptic preservatives are for example selected from triclosan, chlorhexidine and quaternary ammoniums.

Antibiotics can be selected from fusidic acid, penicillin, tetracyclines, pristinamycin, erythromycin, clindamycin, mupirocin, minocycline and doxycycline. In particular, at least one antiviral agent can be used in combination with the antibiotic. This antiviral agent can be acyclovir or valacyclovir.

Preservatives can be selected from the preservatives generally used in cosmetics or nutraceuticals.

Preservatives can further be selected from molecules with anti-bacterial activity, "pseudo-preservatives", such as caprylic derivatives, such as for example the caprayloyl glycine and glyceryl caprylate, such as hexanediol, and sodium levulinate, copper and zinc derivatives, such as gluconate and PCA, phytosphingosine and derivatives of same, benzoyl peroxide, piroctone olamine, zinc pyrithione and selenium sulphide.

The agents that prevent hair loss and/or strengthen the hair and nails can be selected from phytosterols, isoflavones such as for example soya isoflavones, RTH16®, Aminexil®, Minoxidil®, retinol, zinc and derivatives of same, neoruscine, vitamin E, vitamin B2, vitamin B3, vitamin B6, vitamin PP, vitamin B5, also called panthenol or bepanthene, vitamin B8, or vitamin H or biotin, vitamin B9, or folic acid, alpha hydroxy acid, quinine, certain amino acids such as cysteine, cystine, methionone, 5-alpha reductase inhibitors such as finasteride, dutasteride, *Serenoa serrulata* or *repens*, extract of *Cucurbita pepo* or certain phytosterols, keratin, trace elements, mineral salts, certain plant protein or lipid extracts such as for example extracts of pfaffia, sage, lemon, ginseng, quinquina, jojoba, horse chestnut, honey, maize, nettle, echinea, copra, ginseng or coconut.

According to one variant the composition includes only one additional compound.

According to another variant, the composition includes at least two, notably at least three, or at least four additional compounds.

The composition can include two, three, four, five or six additional compounds.

According to one embodiment, the additional components come from the same source, such as for example a single oil or a single extract.

More particularly, the additional compound can be selected from glycyrrhetinic acid, vitamin B3 or niacinamide, isoflavone, such as genistein, corticoids, vitamin E, selenium, beta-carotene, N-acetyl cysteine, vitamin A, vitamin B5, or panthenol, sialic acid, zinc, vitamin C, retinol, hyaluronic acid, caprayloyl glycine, zinc PCA, Minoxidil®, *Serenoa repens*, quinine, vitamin B8 or biotin, and Aminexil® 2,4-diaminopyrimidine-3-oxide, coenzyme QH and coenzyme Q10.

Still more particularly, the composition includes a combination of additional compounds selected from the following combinations: vitamin B3 and vitamin E; vitamin C and hyaluronic acid; isoflavone, such as genistein, vitamin B5, or panthenol, and sialic acid; glycyrrhetinic acid, isoflavone, such as genistein, beta carotene, Minoxidil®, or 6-(1-piperidinyl)pyrimidine-2,4-diamine-3-oxide, quinine, vitamin B8 and Aminexil®, or 2,4-diaminopyrimidine-3-oxide; and retinol, vitamin B3 and hyaluronic acid.

Of course the composition may comprise at least one additional compound from the first variant and at least one additional compound from the second variant.

The content of the additional compound(s) can range from 0.01% to 50% by weight, notably from 0.1% to 35% by weight, in particular from 0.5% to 25% by weight, more particularly from 1% to 25%, still more particularly from 2% to 15%, or from 3% to 10% by weight compared to the total weight of the composition.

According to one embodiment, the unsaponifiable fraction comes from one or more sources that are different from the sources from which the additional compounds arise.

According to another embodiment, the unsaponifiable fraction(s) further include(s) at least one additional compound.

According to a first variant, the compositions are adapted to topical administration and include creams, emulsions, milks, pomades, lotions, oils, aqueous or hydro-alcoholic or glycolic solutions, powders, patches, sprays, sticks or any other product for external application.

According to a second variant, the various preparations are adapted to oral administration. The composition can be provided in the form of gelcaps or capsules, notably soft, in particular gelatine or plant-based, powders, tablets, notably to swallow or chew, or effervescent. It can also be provided in the form of a liquid, emulsion, cream, paste, powder, gel or suspension.

According to a third variant, the composition can be adapted to administration by injection, notably a suspension or an injectable solution.

The unsaponifiable fraction and the additional compound can notably be part of a dietary composition or a dietary supplement. The composition can be provided in the form of the unsaponifiable fraction, for example refined oil enriched in its unsaponifiable fraction, and optionally by the additional compound, as such or on the contrary in the presence of additional compounds, notably one or more excipients.

The composition can include from 10% to 100% by weight of the unsaponifiable fraction and the additional compound.

According to this variant, the unsaponifiable fraction and optionally the additional compound of this invention can be incorporated, without restriction, in foods, beverages and nutraceuticals, including those cited below:

1) Dairy products such as cheeses, butter, milk and other lacteal beverages, mixtures and pastes to be spread containing lacteal products, ice creams and yogurts;
2) Fat-based products such as margarines, pastes to be spread, mayonnaises, fats for cooking, frying oils and vinaigrettes;
3) Cereal-based products composed of grains such as bread and pasta, whether these foods are cooked on the stove, cooked in the oven or processed;
4) Confections such as chocolates, candies, chewing-gum, desserts, toppings, sorbets, glazes, and other fillings;
5) Alcoholic or alcohol-free beverages, including sodas and other soft drinks, fruit juices, dietary supplements, meal substitutes in beverage form such as those sold under the brands Boost™ and Ensure™; and,
6) Various products such as eggs, processed foods such as soups, prepared sauces for pasta, prepared dishes and other similar products.

The composition of the present invention can be incorporated directly and without any other modification to foods, nutraceuticals, protein-rich dietetic products or beverages, for example via techniques such as mixing, infusion, injection, absorption, kneading and pulverisation.

According to one aspect, the invention has as an aim a drug including at least the inventive composition.

According to another aspect, the invention has as an aim the use of the inventive composition for the preparation of a drug.

The drug is notably intended to prevent, treat and/or repair disorders related to the breakdown of connective tissue. It is notably intended to prevent or treat osteoarthritis, gingivitis and periodontopathy and/or to slow, stop, or repair, in whole or part, the damage to connective tissues caused by these diseases.

The optimal modes of administration, dosing schedules and galenic forms of the inventive compounds and compositions can be determined according to criteria generally taken into account in establishing a pharmaceutical treatment, notably a dermatological treatment, or a veterinary treatment adapted to a patient or an animal, such as for example the age or body weight of the patient or animal, overall health, tolerance to the treatment, noted side effects and skin type. According to the type of administration desired, the inventive active composition and/or compounds can further include at least one pharmaceutically acceptable excipient, notably dermatologically acceptable.

According to the first variant, an excipient is used that is adapted for administration by external topical route. The composition according to the present invention can further include at least one pharmaceutical adjuvant known to those persons skilled in the art, selected among thickeners, preservatives, fragrances, colorants, chemical or mineral filters, hydrating agents, thermal water, etc.

The composition including the unsaponifiable fraction and the additional compound having the specifications indicated is particularly intended for cosmetic, dermatological or dietary use. Within the scope of cosmetic or dermatological use, the composition will advantageously be formulated in the form of a preparation adapted to topical administration. Within the scope of dietary use, to nutritive or cosmetic ends ("cosmetic food"), the composition will advantageously be formulated in the form of a preparation adapted to oral administration. It would not include an excipient and would be composed in its entirety of the composition including an unsaponifiable fraction, and optionally an additional compound.

The composition including an unsaponifiable fraction, and optionally an additional compound, is particularly intended for cosmetic or dermatological use. The composition is advantageously formulated in the form of a preparation adapted to topical administration.

The invention also has as an aim the use of an unsaponifiable fraction, and optionally an additional compound, for the manufacture of a dermatological composition or a functional food.

A functional food is a conventional food, or one with such an appearance, which is part of a normal diet, and which has as a characteristic providing beneficial physiological effects that exceed its usual nutritional functions or reducing the risk of chronic diseases.

The dermatological composition or the functional food can be intended to prevent and treat reactions or pathologies due to allergies, inflammation, irritation, or disorders of the skin's barrier or homeostasis and/or of the mucosae and/or of immature, normal or mature integuments.

The invention further relates to a method of cosmetic treatment, hygienic care, improvements and/or a method to perfume mucosae and/or skin that is normal, dry, oily, mixed, dehydrated, aged, sensitive, irritated, uncomfortable, intolerant, exhibiting an imbalance related to ageing that is intrinsic, extrinsic, hormonal or dependent on exogenous events (pollutants, UV, stress, etc.), sensitive to allergies, exhibiting pigmentation disorders, exhibiting an unappealing appearance related to excess body fat, characterised in that it consists in administering a composition or functional food according to the invention.

The invention further relates to a method of treating the integuments (hair and nails) characterised in that it consists in administering a composition or a functional food according to the invention.

In particular, the composition, notably the drug or the functional food, is intended to prevent and treat reactions or pathologies due to allergies, inflammation, irritation or disorders of the barrier or homeostasis of the:

skin, such as acne, atopic dermatitis, eczema, contact dermatitis, irritative dermatitis, allergic dermatitis, seborrheic dermatitis, rosacea (erythro-couperose), psoriasis, vascular disorders, diaper rash, sensitive skin, reactivate skin, dry skin, dehydrated skin, cutaneous erythema, aged or photo-aged skin, pigmented skin (melasma, lentigo, post-inflammatory pigmentation), depigmented skin (vitiligo), skin with cellulite, skin with stretch marks, scurf, dry patches, punctures, cracks notably of the breast, sunburn, inflammation due to rays of all kinds, irritations or allergies (by chemical agents, physical agents (tensile stress: pregnant women), bacteriological agents, fungal or viral agents, parasitic agents (lice, scabies, tinea, acarids, dermatophytes), radiological agents or radiation (UV, IR) or by innate or acquired immune deficiencies, stretch marks, and/or, mucosae such as the periodontium and gums subject to gingivitis (those of newborns, those due to hygiene, tobacco use or other), periodontopathy, or genital mucosae subject to irritations of the male or female external or internal genital areas), and/or, integuments such as nails (broken or fragile nails, etc.) and hair (alopecia, scales, hirsutism, seborrheic dermatitis, folliculitis), immature, normal or mature, notably exhibiting disorders of the scalp such as androgenic alopecia, acute alopecia, localised alopecia, cicatricial alopecia, congenital alopecia, occipital alopecia of newborns, alopecia aerata, due to chemotherapy/radiotherapy or telogen effluvium, anagen effluvium, piliary dystrophy, trichotillomania, tinea or oily or dry scales.

The composition or functional food can also be intended to regenerate tissue and to support scarring, or can also be intended to protect and strengthen the cutaneous barrier, to regulate pigmentation disorders and to act on mechanisms of lipolysis and lipogenesis.

Another advantage of the unsaponifiable fraction and of the additional compound is that it can be used in cosmetics ("food-cosmetic"), more particularly in order to improve cutaneous appearance, to hydrate the skin, to maintain the state of the cutaneous barrier and the intercorneocytic cement by contributing essential fatty acids and sterols, in order to prevent cutaneous ageing by trapping free radicals, and as an anti-inflammatory agent or sun screen.

According to a preferred variant of the invention, the composition including an unsaponifiable fraction, and optionally an additional compound, is used in the treatment of disorders related to dermal tissue. Connective dermal tissue plays a major role as support for the skin, as a shock absorber; the dermis is notably responsible for firmness and flexibility. Degeneration of this tissue, associated with a breakdown of the collagen network (in particular collagens I, III, II and V) or elastic network (elastin—inhibition of synthesis, imperfect synthesis, breakdown of collagen fibres, reduction in the number of fibroblasts and in their metabolism, etc.) can thus have important consequences on:

cutaneous ageing (chronological, extrinsic or photo-ageing and menopausal), notably characterised by a reduction in the number and activity of fibroblasts, as well as an excessive breakdown of the extracellular matrix;

stretch marks, being a consequence of significant damage to fibroblast cells characterised by inhibition of the form of genes coding for fibronectin, collagens I and III and elastin, a phenotypical change of myofibroblasts under the effect of mechanical distensions, all accompanied by inflammation inducing enzymatic breakdown of the dermal matrix. This breakdown of collagenic tissue leads to the formation of an atrophic dermal scar. The principal triggering factors are: mechanical stress, hormonal environment (during pregnancy) and inflammation. Stretch marks affect nearly 50% of youths, primarily females. They are generally observed during pregnancy (60% to 70% of pregnant women), during puberty (25% of girls and 10% of boys), or during certain diseases (metabolic, endocrine and infectious). These are linear lesions, forming a slight depression, narrow, oriented in the direction of cutaneous stress lines and covered with skin folds. Their colour varies according to the developmental stage: they have a red or deep purple colour at the beginning, and then become pearly white in appearance later;

deep wounds reaching the dermis, they cause a breakdown of dermal tissue with a decrease in the number of fibroblasts and a breakdown of the matrix. The scarring mechanism exists to repair damaged tissue: fibroblasts proliferate and the extracellular matrix is restructured by increased synthesis of the various components.

The invention thus has for another aim the use of the composition including an unsaponifiable fraction, and optionally an additional compound, to prevent and/or treat cutaneous ageing, stretch marks and deep wounds. Said composition including an unsaponifiable fraction, and optionally an additional compound, can also support scarring.

According to another advantageous variant of invention, said composition including an unsaponifiable fraction, and optionally an additional compound, can be used to prevent and/or treat subcutaneous atrophies of the dermis. Subcutaneous atrophies are a problem frequently encountered in dermatology. They can be secondary to various aetiologies. According to their location, these lesions represent a minor aesthetic embarrassment or on the contrary severely handicap the person.

Subcutaneous atrophies can have various aetiologies. First and foremost are the cicatricial atrophies either post-traumatic (trauma to the dermis), or post-inflammatory (for example post-acne). Post-traumatic atrophic scars comprise epithelial atrophy with a linear basal membrane testifying to the reorganisation of the dermo-epidermic junction with a loss of papillary pattern. Histologically, the thickness of the dermis is decreased, the collagen fibres are thin and the fibrocytes are often greater in number than in normal skin. Dermal atrophy also comprises pilosebaceous appendage hypotrophy and sometimes sudoral. Scars arising from an inflammatory process are more often constituted in the deep dermis and the hypodermis. There is thickening of the dermis which is accompanied by sclerosis. Components of the extracellular matrix are gradually replaced by thickened and dense collagen fibres. This process of sclerosis is accompanied by a reduction in dermal and appendage vascularization. This stage is one of sclero-atrophies, a state which can be observed in localised scleroderma (morphea). This process can also affect the hypodermis in a context of immune inflammation (severe lupus, Parry-Romberg syndrome), drug-induced (tritherapy, corticoid injections), enzymatic (pancreatic cytosteatonecrosis), or traumatic (atrophy of the hypodermis among women carrying excess weight on the mid-thighs).

Other atrophies include: consecutive to local treatment with dermocorticoids, consecutive to menopause and in combination or not with SHT (substitute hormone therapy), due to certain genetic or non-genetic diseases, hypoplasia, disease of connective tissue of skin collagen, Goltz syndrome, atrophoderma of Pasini and Pierini, atrophic pilar keratosis. Finally, with skin grafts, burns, loss of cutaneous substances of any origin, or bed sores.

It is thus proposed to fill in the atrophy of the dermis by a treatment containing the composition including an unsaponifiable fraction, and optionally an additional compound, which boosts protein activity.

A disturbance of the integrity of the skin can occur in several contexts. The skin can suffer damage during surgeries, burns, radiation, cuts, scratches, friction, and pressure. The severity of the wound varies according to certain factors such as extent, depth and nature. In order to maintain essential functions of the skin, it is very important to repair it when such an event occurs. The healing of a cutaneous wound represents all of the processes that lead to the closing of the wound and to the functional recovery of the cutaneous tissue. The skin is healed by regeneration or re-epithelialisation, in other words it recovers its original structure and functions. Incapable of responding to a lesion by regeneration, the dermis heals by repair, in other words the tissue of origin is replaced by nonspecific connective tissue with, as a result, the formation of a less functional scar (e.g., weaker mechanical resistance). These processes involve different cell populations, distinct cell compartments (epidermis and dermis), various mediators and multiple interactions between all these elements, with the whole varying as a function of time.

According to another advantageous variant of the invention, the aforementioned composition including an unsaponifiable fraction, and optionally an additional compound, can be used to treat, protect and prevent lesions of connective tissues, in particular inflammation of connective tissues, notably osteoarthritis and/or periodontopathy.

According to another aspect, the invention has as an aim the use of at least one unsaponifiable fraction in a composition, notably cosmetic, dermatological, dietary or nutraceutical, as an anti-osteoarthritis agent, anti-gingivitis agent, anti-periodontopathy agent for care of the gums, anti-scarring agent, anti-stretch mark agent, anti-ageing agent, agent against joint problems and discomfort, agent to improve hydration of connective tissues, notably cartilage, periodontium, skin, mucosae and/or integuments.

The examples which follow illustrate the invention but are not restrictive.

EXAMPLES

Example 1

Hydrating Cleanser

| Raw material/Brand name | % (by weight compared to the total weight) |
|---|---|
| Purified water | Qsp 100% |
| Biosaccharide gum | 1% to 5% |
| Butylene glycol | 1% to 5% |
| Sunflower oleodistillate | 0.1% to 5% |
| Hyaluronic acid | 0.1% to 5% |
| Preservatives | 0% to 1% |
| Acid citric monohydrate | 0% to 1% |
| Tromethamine | 0% to 1% |

Example 2

Anti-Ageing Cleanser

| Raw material/Brand name | % (by weight compared to the total weight) |
| --- | --- |
| Capryloyl glycine | 0% to 1% |
| Soda detergent | 0% to 1% |
| Sequestering agent | 0% to 1% |
| Butylene glycol | 1% to 5% |
| Sesame oleodistillate | 0.1% to 5% |
| Extract of *Boswellia serrata* rich in boswellic acid | 0.1% to 5% |
| Preservatives | 0% to 1% |
| Peg-32 | 1% to 5% |
| Peg-7 palmcocoate | 1% to 5% |
| Zinc gluconate | 0% to 1% |
| Citric acid | 0% to 1% |
| Purified water | Qsp 100% |
| Fragrance | 0% to 1% |
| Poloxamer 184 | 1% to 5% |

Example 3

Firming Water-in-Oil Emulsion

| Raw material/Brand name | % (by weight compared to the total weight) |
| --- | --- |
| Liquid isoparaffin | From 5% to 20% |
| Isocetyl stearate | From 5% to 20% |
| Al—Mg hydroxystearate | From 5% to 20% |
| Abil WE 09 | From 1% to 5% |
| Glycerol | From 1% to 5% |
| Vaseline oil | From 1% to 5% |
| Micronised zinc oxide | From 1% to 5% |
| Butylene glycol | From 1% to 5% |
| Maize oleodistillate | From 0.1% to 5% |
| Extract of marine cartilages rich in glycosaminoglycans | From 0.1% to 5% |
| Isononyl isononanoate | From 1% to 5% |
| Beeswax | From 1% to 5% |
| Sodium tartrate | From 1% to 5% |
| Sodium chloride | From 0% to 5% |
| Glycine | From 1% to 5% |
| Preservatives | From 0% to 1% |
| Cholesterol | From 0% to 1% |
| Phytosphingosine | From 0% to 1% |
| Tartaric acid | From 0% to 1% |
| Purified water | Qsp 100% |

Example 4

Youthful Skin Oil-in-Water Emulsion

| Raw material/Brand name | % (by weight compared to the total weight) |
| --- | --- |
| Hydrogenated Polydecene | From 5% to 20% |
| Laurylglucoside-glystearate | From 1% to 5% |
| Dicaprylyl carbonate | From 1% to 5% |
| Glycerol | From 5% to 20% |
| Carbopol | From 0% to 1% |
| Xanthan gum | From 0% to 1% |
| Krill oil | From 0.1% to 5% |
| Carotenoid extract of *Curcuma longa* | From 0.1% to 5% |
| Soda detergent | From 0% to 1% |
| Preservatives | From 0% to 1% |
| Citric acid | From 0% to 1% |
| Purified water | Qsp 100% |

Example 5

Oil for Joint Discomfort

| Raw material/Brand name | % (by weight compared to the total weight) |
| --- | --- |
| Solubilizer | From 0% to 1% |
| Sweet almond oil | From 5% to 20% |
| Caprylate/copra caprate | Qsp 100% |
| Refined macadamia oil | From 5% to 20% |
| Glycerol caprylo caprate | From 5% to 20% |
| Natural alpha bisabolol | From 0% to 1% |
| Alpha tocopherol | From 0% to 1% |
| Avocado and soya unsaponifiable | From 0.1% to 5% |
| Unsaponifiable-rich avocado and soya extract | From 0.1% to 5% |
| Polyphenol extract of mangosteen | From 0.1% to 5% |
| Preservative | From 0% to 1% |
| Ester | From 0% to 1% |

Example 6

Anti-Stretch Marks Milk

| Raw material/Brand name | % (by weight compared to the total weight) |
| --- | --- |
| Sweet almond oil | From 1% to 5% |
| Maize oil | From 1% to 5% |
| Stearic acid | From 1% to 5% |
| C16 C18 cetyl alcohol | From 0% to 1% |
| Antifoaming agent 70414 | From 0% to 1% |
| Lauric alcohol 11oe | From 1% to 5% |
| PEG 300 monolaurate | From 0% to 1% |
| Glycerol monooleate | From 0% to 1% |
| Glycerol monostearate | From 1% to 5% |
| Lupin oleodistillate | From 0.1% to 5% |
| Catechin-rich green tea extract | From 0.1% to 5% |
| Preservatives | From 0% to 1% |
| Citric acid | From 0% to 1% |
| Trisodium citrate | From 0% to 1% |
| Purified water | Qsp 100% |
| Fragrance | From 0% to 1% |
| Groundnut oil | From 1% to 5% |
| Hydrogenated palm nut oil | From 1% to 5% |

Example 7

Well-being Mousse

| Raw material/Brand name | % (by weight compared to the total weight) |
|---|---|
| Purified water | Qsp 100% |
| Lauroamphoacetate | From 5% to 20% |
| Cocoglucoside | From 5% to 20% |
| Surfactant 1 | From 5% to 20% |
| Surfactant 2 | From 5% to 20% |
| PEG 6000 distearate | From 1% to 5% |
| Preservatives | From 1% to 5% |
| Lupin oleodistillate | From 0.1% to 5% |
| Echium oil of | From 0.1% to 5% |
| Camomile extract | From 1% to 5% |
| Citric acid monohydrate | From 0% to 1% |
| Sequestering agent | From 0% to 1% |
| Fragrance | From 0% to 1% |
| Soda detergent | From 0% to 1% |

Example 8

Repairing Spray

| Raw material/Brand name | % (by weight compared to the total weight) |
|---|---|
| Purified water | Qsp 100% |
| Trilaureth-4 phosphate | From 1% to 5% |
| Dicaprylyl carbonate | From 1% to 5% |
| Butylene glycol | From 1% to 5% |
| Erythrityl ester | From 1% to 5% |
| Liquid Vaseline oil | From 1% to 5% |
| Shea butter | From 0% to 1% |
| Vegetable oil | From 0% to 1% |
| Preservatives | From 0% to 1% |
| Sunflower oleodistillate | From 0.1% to 5% |
| *Rosa canina* extract rich in mono- and di-glycerol glycosides | From 0.1% to 5% |
| Soda detergent | From 0% to 1% |
| Fragrance | From 0% to 1% |
| Xanthan gum | From 0% to 1% |
| Carbopol | From 0% to 1% |
| Sequestering agent | From 0% to 1% |
| Citric acid | From 0% to 1% |

Example 9

Photoprotector Stick

| Raw material/Brand name | % (by weight compared to the total weight) |
|---|---|
| Castor oil | Qsp 100% |
| Oleic alcohol | From 10% to 20% |
| Palm nut oil | From 10% to 20% |
| Polyglycerin-3-beeswax | From 10% to 20% |
| Candelilla wax | From 10% to 20% |
| Hectorite | From 10% to 20% |
| Titanium dioxide | From 0% to 5% |
| Lupin oleodistillate | From 0.1% to 5% |
| *Awara* oil | From 0.1% to 5% |
| Shea butter | From 0% to 5% |
| Vitamin E | From 0% to 1% |

Example 10

SPF 50+Sun Lotion

| Raw material/Brand name | % (by weight compared to the total weight) |
|---|---|
| Purified water b4 | Qsp 100% |
| Titanium oxide | From 10% to 20% |
| Cyclopentasiloxane | From 5% to 15% |
| Octyl palmitate | From 5% to 15% |
| C12-c15 alkyl benzoate | From 5% to 10% |
| Decyl pentanoate | From 5% to 10% |
| Zinc oxide | From 5% to 10% |
| Glycerol | From 1% to 5% |
| PEG-45/dodecyl glycol copolymer | From 1% to 5% |
| Sesame oleodistillate | From 0.1% to 5% |
| Yeast extract rich in vitamin B | From 0.1% to 5% |
| Sodium chloride | From 1% to 5% |
| Dextrin palmitate | From 1% to 2% |
| Vitamin E | From 0% to 2% |
| Preservatives | From 0% to 2% |
| Guar hydroxypropyl | From 0% to 1% |
| *Aloe vera* | From 0% to 1% |
| Soda detergent | From 0% to 1% |
| EDTA 2 Na | From 0% to 1% |
| Zinc gluconate | From 0% to 1% |

Example 11

SPF 50+Sun Spray

| Raw material/Brand name | % (by weight compared to the total weight) |
|---|---|
| Glycerol caprylo caprate | From 5% to 20% |
| Cyclopentasiloxane | From 10% to 20% |
| Dicaprylyl carbonate | From 5% to 20% |
| Tinosorb S | From 1% to 10% |
| Titanium oxide 100 | From 10% to 20% |
| Hectorite | From 0% to 5% |
| Alpha tocopherol | From 0% to 2% |
| Laurylglucoside-glystearate | From 0% to 10% |
| Purified water b4 | Qsp 100% |
| Citric acid | From 0% to 2% |
| Pentylene glycol | From 0% to 5% |
| Glycerol | From 0% to 5% |
| Xanthan gum | From 0% to 2% |
| Sunflower oleodistillate | From 0.1% to 5% |
| Green coffee extract rich in chlorogenic acids | From 0.1% to 5% |
| *Aloe vera* | From 0% to 1% |
| Zinc gluconate | From 0% to 1% |
| Preservatives | From 0% to 2% |
| Tinosorb M | From 1% to 10% |

Example 12

Youthful Skin Cleansing Cream

| Raw material/Brand name | % (by weight compared to the total weight) |
|---|---|
| Purified water | Qsp 100% |
| Arlatone | From 10% to 30% |
| Cocoglucoside | From 5% to 20% |

-continued

| Raw material/Brand name | % (by weight compared to the total weight) |
|---|---|
| Guar hydroxypropyl | From 1% to 5% |
| Glycine capryloyl | From 0% to 2% |
| Preservatives | From 0% to 2% |
| Fragrance | From 0% to 1% |
| Citric acid | From 0% to 1% |
| Zinc PCA | From 0% to 1% |
| Lupin oleodistillate | From 0.1% to 5% |
| Extract of ginger rich in gingerol and shogaol | From 0.1% to 5% |

Example 13

Matt Anti-Ageing Emulsion

| Raw material/Brand name | % (by weight compared to the total weight) |
|---|---|
| PEG 40 stearate | From 1% to 5% |
| PEG 5 glyceryl stearate | From 1% to 5% |
| Ceresin wax | From 1% to 5% |
| Glycerol monostearate | From 1% to 5% |
| Sorbitan stearate | From 0% to 2% |
| Cetyl alcohol | From 0% to 2% |
| Di-malate alcohol | From 5% to 20% |
| Vitamin E | From 0% to 1% |
| 5 alpha avocuta | From 1% to 5% |
| Sesame oleodistillate | From 0.1% to 5% |
| Butylene glycol | From 1% to 5% |
| Extract of goji berry rich in oligosaccharides | From 0.1% to 5% |
| Piroctolamine | From 0% to 1% |
| Preservatives | From 0% to 1% |
| Glycerol | From 1% to 10% |
| Xanthan gum | From 0% to 1% |
| Zinc PCA | From 0% to 2% |
| Rice starch | From 1% to 5% |
| Nylon 6 | From 0% to 2% |
| Polyacrylamide gel | From 1% to 5% |
| Vitamin B6 | From 0% to 1% |
| Fragrance | From 0% to 1% |
| Purified water | Qsp 100% |

Example 14

Smoothing and Hydrating Emulsion

| Raw material/Brand name | % (by weight compared to the total weight) |
|---|---|
| Isononyl isononanoate | From 1% to 10% |
| Isocetyl stearate | From 1% to 10% |
| PEG 40 stearate | From 1% to 5% |
| PEG 5 glyceryl stearate | From 1% to 5% |
| Preservatives | From 0% to 1% |
| C16 C18 cetyl alcohol | From 0% to 2% |
| PPG/SMDI polymer | From 0% to 1% |
| Salicylic acid | From 0% to 2% |
| Squalane gel | From 0% to 2% |
| Dioctyl ether | From 1% to 10% |
| Di-malate alcohol | From 1% to 10% |
| Sunflower extract | From 1% to 10% |
| Tromethamine | From 1% to 5% |
| Butylene glycol | From 1% to 10% |
| Trisodium citrate | From 0% to 1% |
| Sclerotium gum | From 0% to 1% |
| Rice starch | From 1% to 10% |

-continued

| Raw material/Brand name | % (by weight compared to the total weight) |
|---|---|
| Polyacrylamide gel | From 0% to 1% |
| Vitamin | From 0% to 2% |
| Glycine | From 0% to 2% |
| Fragrance | From 0% to 1% |
| Vitamin E | From 0% to 2% |
| Citric acid | From 0% to 1% |
| Avocado and soya unsaponifiables | From 0.1% to 5% |
| Hyaluronic acid | From 0.1% to 5% |
| Purified water | Qsp 100% |

Example 15

Youthful Skin Exfoliant

| Raw material/Brand name | % (by weight compared to the total weight) |
|---|---|
| Arlatone DUO | From 5% to 20% |
| Exfoliating agent | From 1% to 10% |
| Sclerotium gum | From 1% to 10% |
| Preservatives | From 0% to 1% |
| Glycine capryloyl | From 0% to 1% |
| Soda | From 0% to 1% |
| Maize oleodistillate | From 0.1% to 5% |
| Capsaicin-rich pepper extract | From 0.1% to 5% |
| Sequestering agent | From 0% to 1% |
| Citric acid | From 0% to 1% |
| Purified water | Qsp 100% |
| Fragrance | From 0% to 1% |

Example 16

Joint Discomfort Capsule

| | |
|---|---|
| Canola oleodistillate | 170 mg |
| Vitamin K2 oil | 30 mg |
| Krill oil | 300 mg |
| Haref oil | 10 mg |
| Vitamin E | |
| Beeswax | |
| Soya lecithin | |
| Dietary gelatine | |
| Glycerin | QSP 1 softcap |

This composition can be administered in 2 to 4 capsules of 760 mg per day.

Example 17

Joint Comfort Gelcap

| | |
|---|---|
| Avocado/soya unsaponifiables | 600 mg |
| Coenzyme Q10 | 30 mg |
| Fish oil | 300 mg |
| Krill oil | 100 mg |
| Vitamin E | |
| Beeswax | |
| Soya lecithin | |
| Dietary gelatine | |
| Glycerin | QSP 1 gelcap |

Example 18

Joint Comfort Gelcap

| | |
|---|---|
| Soya and clover isoflavones | 300 mg |
| Green tea/grape or pine polyphenol | 30 mg |
| Brown algae oil | 300 mg |
| Krill oil | 100 mg |
| Vitamin E | |
| Beeswax | |
| Soya lecithin | |
| Dietary gelatine | |
| Glycerin | QSP 1 gelcap |

Example 19

Joint Comfort Gelcap

| | |
|---|---|
| *Harpagophytum* | 300 mg |
| Gold nano dispersion | 30 mg |
| Hazel nut oil | 300 mg |
| Curcumin | 100 mg |
| Lignan | 100 mg |
| Beeswax | |
| Soya lecithin | |
| Dietary gelatine | |
| Glycerin | QSP 1 gelcap |

Example 20

Joint Comfort Gelcap

| | |
|---|---|
| Avocado and soya unsaponifiables | 600 mg |
| Hyaluronic acid | 30 mg |
| Diacerein or rhubarb extract | 300 mg |
| Krill oil | 100 mg |
| Vitamin E | |
| Beeswax | |
| Soya lecithin | Qsp 1 gelcap |

Example 21

Anti-Arthrosis Gelcap

| | |
|---|---|
| Avocado and palm unsaponifiables | 300 mg |
| Non-steroidal anti-inflammatory | 30 mg |
| Extract of *Morinda citrifolia* | 300 mg |
| Lupin extract | 100 mg |
| Vitamin E | |
| Beeswax | |
| Soya lecithin | |
| Glycerin | QSP 1 gelcap |

Example 22

Anti-Arthrosis Gelcap

| | |
|---|---|
| Avocado and soya unsaponifiables | 300 mg |
| Melatonin | 30 mg |
| Guggulipid | 300 mg |
| *Perna canaliculus* | 100 mg |
| Resveratrol | 5 mg |
| Methyl sulfonylmethane | 50 mg |
| S-adenosyl methionine | 100 mg |
| Beeswax | |
| Soya lecithin | |
| Glycerin | QSP 1 gelcap |

Example 23

Anti-Arthrosis Gelcap

| | |
|---|---|
| Avocado and soya unsaponifiables | 300 mg |
| Strontium ranelate | 30 mg |
| Beeswax | |
| Soya lecithin | |
| Glycerin | QSP 1 gelcap |

Example 24

Anti-Arthrosis Gelcap

| | |
|---|---|
| Avocado and soya unsaponifiables | 300 mg |
| Parthenolide | 30 mg |
| Biphosphonate | 50 mg |
| Beeswax | |
| Soya lecithin | |
| Glycerin | QSP 1 gelcap |

Example 25

Anti-Arthrosis Gelcap

| | |
|---|---|
| Avocado and soya unsaponifiables | 50 mg |
| Phytoecdysone | 10 mg |
| Xianlinggbuao | 5 mg |
| Primorine | 10 mg |
| Extract of *Garcinia cola* | 5 mg |
| Extracted of *Whithania somnifera* | 5 mg |
| Extract of *Phellodendron* | 5 mg |
| Extract of *Clematis manshurica* | 5 mg |
| Extract of ginger | 10 mg |
| Extract of *Centella asiatica* | 10 mg |
| Extract of *Alpinia galanga* | 10 mg |
| Calcium pentosan sulphate | 10 mg |
| Extract of *Ecklonia cava* | 5 mg |
| Linoleic and linolenic acid | 100 mg |
| Cysteine | 1 mg |
| Fullerene | 10 mg |
| Citrus flavonoids | 5 mg |
| Mineral salts | 15 mg |
| Willow bark extract | 5 mg |
| *Opuntia ficus-indica* extract (polysaccharides) | 100 mg |

-continued

| | |
|---|---|
| Mannosamine | 25 mg |
| Beeswax | |
| Soya lecithin | |
| Glycerin | QSP 1 gelcap |

Example 26

Cutaneous Hydration Capsule

| | |
|---|---|
| Sunflower oleodistillate | 30 mg |
| Cereal oil rich in ceramides and polar lipids | 300 mg |
| Oil of lupin | 50 mg |
| Vitamin E | QSP 100% RDA |
| Vitamin C | QSP 50% RDA |
| Beeswax | |
| Soya lecithin | |
| Dietary gelatine | |
| Glycerin | QSP 1 softcap |

This composition can be administered in 4 to 6 capsules of 500 mg per day.

Example 27

Integument beauty tablets

| | |
|---|---|
| Sesame oleodistillate | 25 mg |
| Cereal extracts (maize, buckwheat, millet, spelt) rich in sulphur amino acids | 200 mg |
| Vitamin C | QSP 50% RDA |
| Glycosaminoglycans from fish cartilages | 200 mg |
| Glucidex IT 19 (compression agent) | QSP 1 800 mg tablet |

This composition can be administered in 5 to 8 tablets per day.

Example 28

Cutaneous Anti-Ageing Tablet

| | |
|---|---|
| Canola oleodistillate | 200 mg |
| Cereal extracts (maize, buckwheat, millet, spelt) rich in sulphur amino acids | 200 mg |
| Zn in chelate form | QSP 100% RDA |
| Vitamin C | QSP 50% RDA |
| Glycosaminoglycans from fish cartilages | 200 mg |
| Fruit flavour (citrus, red fruit), potassium acesulfame, Glucidex IT 19 (compression agent) | QSP 1 2000 mg tablet |

This composition can be administered once per day.

Example 29

Cutaneous Anti-Ageing Tablet

| | |
|---|---|
| Palm oleodistillate | 200 mg |
| Cereal extracts (maize, buckwheat, millet, spelt) rich in sulphur amino acids | 200 mg |
| Zn in chelate form | QSP 100% RDA |
| Vitamin C | QSP 50% RDA |

-continued

| | |
|---|---|
| Glycosaminoglycans from fish cartilages | 200 mg |
| Hyaluronic acid | 200 mg |
| Fruit flavour (citrus, red fruit), potassium acesulfame, Glucidex IT 19 (compression agent) | QSP 1 2000 mg tablet |

Example 30

Stick Powder—Youthful Skin

| | |
|---|---|
| Lupin oleodistillate | 100 mg |
| Polyphenol-rich tea extract | 100 mg |
| OPC-rich grape extract | 50 mg |
| Betaglucans of plant origin | 100 mg |
| Xanthan gum | 1 mg |
| Sodium ascorbate | 0.3 mg |
| Maltodextrin | QSP 5 g |

This composition can be administered 2 times per day.

Example 31

Stick Powder for Joint Discomfort

| | |
|---|---|
| Avocado/soya unsaponifiable | 100 mg |
| Extract of Centella asiatica | 100 mg |
| Magnesium, selenium, manganese | QSP 100% RDA |
| Xanthan gum | 1 mg |
| Sodium ascorbate | 0.3 mg |
| Maltodextrin | QSP 5 g |

This composition can be administered 2 times per day.

Example 32

Anti-Ageing Chocolate-Flavoured Cereal Bar

| | |
|---|---|
| Sesame oleodistillate | 200 mg |
| Lycopene | 6 mg |
| Astaxanthin | 4 mg |
| Fucoxanthin | 4 mg |
| Micro-encapsulated lutein | 4 mg |
| Micro-encapsulated tocotrienol | QSP 100% vitamin E RDA |
| Dark Chocolate, oligofructose, sugar, fructose syrup, fat-reduced cocoa powder, crunchy cereals, powdered skim milk, almonds, glycerol, sorbitol, plant oils, glucose syrup, flavouring, sweetened condensed milk, soya lecithin, fatty acid mono- and di-glycerides, caramelised syrup, maltodextrin, salt, potassium sorbate, alpha tocopherol | QSP 1 50 g bar |

This composition can be administered once per day.

Example 33

Youthful Skin Vanilla-Flavoured Cereal Bar

| | |
|---|---|
| Sunflower oleodistillate | 200 mg |
| Cereal extracts (maize, buckwheat, millet, spelt) rich in sulphur amino acids | 200 mg |

| | |
|---|---|
| Glycosaminoglycans from fish cartilages | 200 mg |
| Polyphenol-rich green tea extract | 200 mg |
| Oligofructose, sugar, fructose syrup, crunchy cereals, powdered skim milk, almonds, glycerol, sorbitol, plant oils, glucose syrup, flavouring, sweetened condensed milk, soya lecithin, fatty acid mono- and di-glycerides, caramelised syrup, maltodextrin, salt, potassium sorbate, alpha tocopherol | QSP 1 50 g bar |

This composition can be administered once per day.

Example 34

Praline-Flavoured Lacteal Drink for Joint Discomfort

| | |
|---|---|
| Avocado/soya unsaponifiable | 300 mg |
| Polyphenol-rich green tea extract | 100 mg. |
| Group B vitamin (B1, B2, B3, B5, B6, B9, B12) | QSP 100% RDA |
| Zn, Mg, Se | QSP 100% RDA |
| Powdered skim milk, flavouring, fructose, egg white, hazel nuts, sugar, caramel, beta-carotene, xanthan gum, aspartame, potassium acesulfame, soya lecithin, maltodextrin | QSP 1 30 g packet |

This composition can be administered once per day.

Example 35

Mint-Flavoured Chewing-Gum or Chewable Tablet for Care of the Gums

| | |
|---|---|
| Sorbitol | 141 mg |
| Xilitol | 50 mg |
| Mannitol | 200 mg |
| Aspartame | 10 mg |
| Acesulfame K | 5 mg |
| Sucralose | 20 mg |
| Gum base | 500 mg |
| Talc | 8 mg |
| Magnesium stearate | 5 mg |
| Lupin oleodistillate | 50 mg |
| Green tea extract | 200 mg |
| Cranberry extract | 120 mg |
| Gum arabic | 5 mg |
| Modified starch | 3 mg |
| Soya lecithin | 3 mg |
| Colorant | QSP chosen colour |

This composition can be administered 3 times per day after each meal.

Example 36

Oral Gingivitis Spray

| | |
|---|---|
| Ethanol | 1 to 5 g |
| Glycerin | 1 to 10 g |
| Sodium saccharinate | 0.1 to 1 g |
| Avocado soya unsaponifiable | 0.1 to 5 g |
| Catechin-rich green tea extract | 0.1 to 5 g |
| Potassium sorbate | 0 to 2 g |
| Cremophor RH 40 | 1 to 5 g |
| Aroma | 0.5 to 3 g |
| Chlorhexidine gluconate | 0.1 to 1 g |
| Citric acid | 0 to 1 g |
| Purified water | Qsp 100 g |

Example 37

Activity Evaluation Protocol

Thin slices of cartilage of patients suffering from osteoarthritis were excised while avoiding the calcified layer. They were washed several times in DMEM medium containing HEPES, penicillin and streptomycin. The slices of cartilage were then cut into small fragments of a few cubic millimeters.

Chondrocytes were then isolated from the extracellular matrix by a succession of enzymatic digestions. The cartilage fragments were incubated at 37° C. under constant agitation in the basic medium with, successively, hyaluronidase, pronase E and finally with clostridial collagenase.

The cells were then filtered through a 70 μm nylon membrane, washed with DMEM and counted using a Neubauer plate. At this point, the cell viability estimated by the trypan blue exclusion test was higher than 95%.

The cells were cultured in 12-well plates. The culture medium was composed of basic medium enriched with 10% foetal bovine serum. After 3 days the chondrocytes were quite adherent and confluent, and the cells were then rinsed with PBS and cultivated for 24 h in basic medium supplemented with ascorbic acid, ITS+proline glutamine. The chondrocytes were then cultivated for 48 h in the same medium, in the presence or absence of 10 μg/ml of composition 1, 2, 3 or 4 or combinations of these compositions (2+4 and 1+3).

The cultures were prepared in the presence or absence of $10^{-11}$ M recombinant human IL-1β.

The cultures were maintained at 37° C. in an atmosphere of 95% air and 5% $CO_2$. At the end of the incubation period, the culture media were taken and stored at −20° C. until they were analysed. At the end of culturing, the chondrocytes were rinsed with PBS and then detached from their culture support by treatment with trypsin, recovered by centrifugation and finally washed with 0.05 M, pH 7.4 TRIS buffer and then dissociated by ultrasound at 4° C.

Deoxyribonucleic acid (DNA) was quantified according to the technique of Labarca and Paigen (Labarca C. and Paigen K. A simple, rapid, and sensitive DNA assay procedure, Anal Biochem, 1980. 102: 344-52). This method is based on the principle of fluorescence emitted by a reagent, bis-benzimidazole, when it binds to DNA. The technique was applied directly to the cell extracts. The reference curve was prepared from human placenta DNA. Suitable dilutions were then prepared in order to obtain solutions of increasing DNA concentrations (0, 0.625, 1.25, 2.5, 5, 10 and 20 μg/ml). The bis-benzimidazole solution was then added to the cell extracts or to the reference solutions. After 1 h of incubation, the samples were read with a fluorometer using an excitation wavelength of 356 nm and an emission wavelength of 458 nm.

IL-6 in the culture media was assayed by EASIA (solid phase enzyme amplified sensitivity immunoassay). These assays are based on an oligoclonal system comprised of two monoclonal antibodies directed against distinct epitopes of the molecule tested. The antigen reacts with the antibodies fixed on the bottom of a 96-well plate and with antibodies coupled to biotin. After an incubation period allowing the formation of biotinylated antibody-antigen-antibody complexes, the plates are washed with washing buffer (TWEEN 20/HEPES). A streptavidin-peroxidase solution is added and incubated for 30 minutes. The plate is again washed and the antibodies bound to the antigen are revealed by adding a solution of tetramethylbenzidine (TMB) and $H_2O_2$. After 30 minutes of incubation, the reaction is quenched by adding 1.8 N $H_2SO_4$ and absorbance is read at 450 nm.

$PGE_2$ present in the culture media was assayed by a radio-immunoassay (RIA). Polyclonal antiserum, obtained from rabbit, does not have a cross-reaction with other prostanoids ($TxB_2$, 6-keto-PGF-1α, $PGA_2$) or with fatty acids (arachidonic, linoleic, oleic acid). Tracer ($^3$H-$PGE_2$) is solubilised in acetonitrile and diluted in order to obtain 10,000 cpm/100 μl. The incubation buffer consists of 0.01 M TRIS, 500 mg/l azide ($NaN_3$), 9 g/l NaCl and 1 g/l gelatin. The incubation volume is composed of tracer (±10,000 cpm), antiserum and the reference preparation or the sample. The reference curve is obtained by diluting a solution of $PGE_2$ in order to obtain a series of concentrations ranging between 19 and 5000 pg/ml. After 48 h of incubation at 4° C., the free fraction of antigen is separated from the antigen-antibody complexes by adding a solution of 0.5% charcoal and 0.5% dextran T70. After 15 minutes of incubation at 4° C., the sample tubes are centrifuged for 20 minutes at 3,300 rpm at 4° C. The supernatant is recovered, mixed with scintillation fluid and counted on a β meter. The intra- and inter-assay variation coefficients are 6% and 10%, respectively. The limit of detection is 19 pg/ml.

Mean (X) and standard deviation were calculated for each culture condition. The means obtained were compared using the Student's t-test.

Example 36a

Effect of a Composition Including a Canola Concentrate in Combination with a Composition Comprised of Vitamin K2 by Measurement of E2 Prostaglandin Production The $PGE_2$ production of arthrosis chondrocytes was measured on the basis of the protocol described above.

Under basal conditions, the chondrocytes produced 9±4 pg of $PGE_2$ per μg of DNA after 48 h of culture.

When the culture medium includes 10 μg/ml of a composition comprised of a canola concentrate (composition 2), or when it includes 10 μg/ml of a composition comprised of vitamin K2 (composition 4), the quantity of $PGE_2$ produced remains constant.

On the other hand, when the culture medium includes 10 μg/ml of a composition comprised of canola concentrate (composition 2) and 10 μg/ml of a composition comprised of vitamin K2 (composition 4), the quantity of $PGE_2$ produced decreases by 76%, p<0.05.

Since the production of $PGE_2$ is related to the degree of inflammation of connective tissues, this example clearly shows an anti-inflammatory effect of the inventive composition.

Example 36b

Effect of a Composition Including ⅓ Avocado Oil, ⅔ Soya Total Unsaponifiable in Combination with a Composition Comprised of Krill Oil by Measurement of Interleukin 6 (IL-6)

The production of IL-6 arthrosis chondrocytes was measured on the basis of the protocol described above.

Under basal conditions, IL-6 production was below the limit of detection of the assay. In the presence of IL-1β, this production was of 23,335±1,529 pg/μg of IL-6 DNA.

When the culture medium includes 10 μg/ml of a composition comprised of ⅓ avocado oil and ⅔ soya total unsaponifiable (composition 1), or when it includes 10 μg/ml of a composition comprised of krill oil (composition 3), chondrocyte IL-6 production remains constant.

However, when the culture medium includes 10 μg/ml of a composition comprised of ⅓ avocado oil and ⅔ soya total unsaponifiable (composition 1) and 10 μg/ml of a composition comprised of krill oil (composition 3), a 15% (p<0.05) reduction in chondrocyte IL-6 production is noted.

Since IL-6 production is related to the degree of inflammation of connective tissues, this example clearly shows an anti-inflammatory effect of the inventive composition.

The invention claimed is:

1. A composition, comprising krill oil and a concentrate of an oil of avocado, canola, maize, sunflower, sesame, lupin, or soya, wherein the content of the unsaponifiable fraction in the concentrate is 5% to 20% by weight compared to the total weight of the composition.

2. The composition according to claim 1, wherein the concentrate is a concentrate of an oil of canola.

3. The composition according to claim 1, wherein the composition further comprises at least one avocado and soya total unsaponifiable.

4. The composition according to claim 1, wherein the composition is a dietary or nutraceutical composition, a food, a cosmetic, a pharmaceutical or a dermatological composition.

5. The composition according to claim 1, wherein the content of the krill oil ranges from 0.01% to 50% by weight compared to the total weight of the composition.

6. The composition according to claim 1, wherein the composition is adapted to topical administration, comprising creams, emulsions, milks, pomades, lotions, oils, aqueous or hydro-alcoholic or glycolic solutions, powders, patches, sprays, or sticks.

7. The composition according claim 1, wherein the composition is adapted to oral administration.

8. The composition of claim 5, wherein the content of the krill oil ranges from 0.1% to 35% by weight compared to the total weight of the composition.

9. The composition of claim 8, wherein the content of the krill oil ranges from 0.5% to 25% by weight compared to the total weight of the composition.

10. The composition of claim 9, wherein the content of the krill oil ranges from 1% to 25% by weight compared to the total weight of the composition.

11. The composition of claim 10, wherein the content of the krill oil ranges from 2% to 15% by weight compared to the total weight of the composition.

12. The composition of claim 11, wherein the content of the krill oil ranges from 3% to 10% by weight compared to the total weight of the composition.

13. The composition of claim 7, wherein the composition is provided in the form of gelcaps or soft gelatine or plant-based capsules, powders, or tablets, and wherein the composition is to swallow or chew or effervescent, or to administration by injection.

14. A method of cosmetic treatment comprising administering to a subject in need thereof the composition according to claim 1.

15. The method of claim 14, wherein the cosmetic treatment is hygienic care, hydration, or improving the appearance of skin, mucosae and/or integuments.

* * * * *